(12) United States Patent
Binder et al.

(10) Patent No.: US 6,238,714 B1
(45) Date of Patent: May 29, 2001

(54) FEEDSTUFF ADDITIVE WHICH CONTAINS D-PANTOTHENIC ACID AND/OR ITS SALTS AND A PROCESS FOR THE PREPARATION THEREOF

(75) Inventors: Michael Binder, Steinhagen (Westf.); Klaus-Erich Uffmann; Iiona Walger, both of Bielefeld; Ulrich Becker, Selce; Walter Pfefferle, Halle(Westf.); Heinz Friedrich, Hanau, all of (DE)

(73) Assignee: Degussa-Huls AG, Frankfurt Am Main (DE)

( * ) Notice: Subject to any disclaimer, the term of this patent is extended or adjusted under 35 U.S.C. 154(b) by 0 days.

(21) Appl. No.: 09/431,097

(22) Filed: Nov. 1, 1999

(30) Foreign Application Priority Data

May 5, 1999 (DE) ............................... 199 20 507

(51) Int. Cl.[7] ..................................... A23L 1/302
(52) U.S. Cl. ............................ 426/72; 426/74; 426/807; 426/656
(58) Field of Search ..................... 426/656, 807, 426/74, 72

(56) References Cited

U.S. PATENT DOCUMENTS

| | | | |
|---|---|---|---|
| 2,918,370 | * 12/1959 | Helgren | 99/2 |
| 3,862,337 | * 1/1975 | Osborne | 426/2 |
| 4,552,775 | * 11/1985 | Baeling et al. | 426/624 |
| 5,133,976 | * 7/1992 | Rovy | 426/2 |
| 5,431,933 | * 7/1995 | Binder et al. | 426/60 |
| 5,518,906 | * 5/1996 | Hikichi et al. | 435/116 |
| 5,622,710 | * 4/1997 | Binder et al. | 424/438 |
| 5,840,358 | * 11/1998 | Hofler et al. | 426/467 |

FOREIGN PATENT DOCUMENTS

| | | |
|---|---|---|
| 598177 | 2/1948 | (GB). |
| 784434 | 10/1957 | (GB). |
| 9633283 | * 10/1996 | (WO). |
| 9736996 | * 10/1997 | (WO). |

OTHER PUBLICATIONS

Eggeling et al., "The Fruits of Molecular Physiology: Engineering the L–Isoleucine Biosynthesis Pathway in *Corynebacterium Glutamicum*", Journal of Biotechnology 56 (1997), pp. 167–182.

* cited by examiner

Primary Examiner—Chhaya D. Sayala
(74) Attorney, Agent, or Firm—Pillsbury Winthrop LLP

(57) ABSTRACT

The invention provides a feedstuff additive based on a fermentation broth which is obtained by the fermentation of D-pantothenic acid producing microorganisms and contains one or more salts of D-pantothenic acid, selected from the group of sodium, potassium, ammonium, magnesium or calcium salts.

11 Claims, No Drawings

FEEDSTUFF ADDITIVE WHICH CONTAINS D-PANTOTHENIC ACID AND/OR ITS SALTS AND A PROCESS FOR THE PREPARATION THEREOF

FIELD OF THE INVENTION

The invention relates to an animal feedstuff additive based on a fermentation broth, which contains D-pantothenic acid and/or one of its salts and a process for preparing this additive.

BACKGROUND OF THE INVENTION

Pantothenic acid is produced all over the world on a scale of several thousand tonnes per year. A large part of the pantothenic acid produced is used for feeding economically useful animals such as poultry and pigs. Demand is increasing.

Pantothenic acid may be prepared by chemical synthesis or biotechnically by the fermentation of suitable microorganisms in suitable nutrient solutions. In the case of chemical synthesis, DL-pantolactone is an important precursor. It is prepared in a multi-stage process from formaldehyde, isobutylaldehyde and cyanide. In further process steps, the racemic mixture is separated and D-pantolactone is condensed with β-alanine, thus producing D-pantothenic acid.

The typical commercial form is the calcium salt of D-pantothenic acid. The calcium salt of the racemic mixture of D,L-pantothenic acid can also be used.

The advantage of fermentative preparation using microorganisms is the direct formation of the desired stereoisomeric form, that is the D-form, which contains no L-pantothenic acid.

Various types of bacteria such as, for example, *Escherichia coli, Arthrobacter ureafaciens, Corynebacterium erythrogenes, Brevibacterium ammoniagenes* and also yeasts such as, for example, *Debaromyces castellii* may, as shown in EP-A-0 493 060, EP-A-0 590 857 and WO 97/10340, produce D-pantothenic acid under suitable conditions of fermentation. Particularly suitable microorganisms are the derivatives of *Escherichia coli* IF03547 described there, such as e.g. the strains FV5069/pFV31 or FV5069/pFV202.

During the fermentative preparation of D-pantothenic acid, as described in EP-A-0 493 060, EP-A-0 590 857 and WO 97/10340, a microorganism capable of D-pantothenic acid production is cultivated in a suitable nutrient and the D-pantothenic acid produced is then isolated in a costly manner, purified and prepared as the calcium salt.

Suitable nutrient media contain a source of carbon such as e.g. glucose or starch flour hydrolysate or sucrose or molasses, precursors such as e.g. β-alanine, D,L-pantoic acid or D,L-pantolactone, a source of nitrogen such as e.g. ammonium sulfate, a source of phosphorus such as e.g. potassium phosphate and other salts, trace elements and vitamins and optionally complex media additives such as e.g. yeast extract. The microorganisms are then incubated in this medium at a suitable pH, with appropriate aeration and stirring, wherein these then excrete D-pantothenic acid.

According to the current prior art, which is represented by WO96/33283 and EP-A-0 590857, the calcium salt of D-pantothenic acid is obtained from the pantothenic acid-containing fermentation broth by costly isolation and purification. After initial isolation of the biomass by filtering or centrifuging, further processing of the filtrate is performed by purification using active carbon or column chromatography. After reaction of the solutions obtained in this way with calcium hydroxide, the desired Ca salt crystallises out.

According to WO 96/33283 the filtrate is decoloured with active carbon in the first column. The pH is adjusted to 3.0 with concentrated hydrochloric acid and the liquid is then continuously purified over two further columns packed with active carbon. Elution of the D-pantothenic acid is achieved with the aid of methyl alcohol. After the subsequent neutralisation step using $Ca(OH)_2$ powder, a solution is obtained from which calcium D-pantothenate is recovered by crystallisation at 5° C.

In the method described in EP-A-0 590 857, the filtrate is first purified with the aid of cation and anion exchanger columns. Elution is performed with hydrochloric acid. The eluted fraction is then neutralised with $Ca(OH)_2$, active carbon is added thereto and the mixture is filtered. The filtrate obtained is then extracted into a low molecular weight alcohol (methanol, ethanol, isopropanol) and calcium D-pantothenate is obtained by crystallisation.

The calcium D-pantothenate prepared in the way described above is used as an additive in feedstuffs for animal nutrition.

SUMMARY OF THE INVENTION

According to the prior art, salts of D-pantothenic acid and D,L-pantothenic acid are prepared by reacting the acid, prepared by chemical synthesis or fermentation, with the desired salt solutions.

The object of the invention is to provide new preparative forms of D-pantothenic acid and its salts which are suitable as feedstuff additives.

Furthermore, an object of the invention is to provide a method of preparation which is more economical and more efficient than the currently known processes.

DESCRIPTION OF THE INVENTION

The invention provides an animal feedstuff additive based on a fermentation broth, characterised in that it contains
a) D-pantothenic acid and/or its salts,
b) the biomass formed during fermentation in an amount of 0 to 100% and
c) at least the greater part of the other dissolved ingredients of the fermentation broth and
d) is present in solid form, in particular in a finely divided and free-flowing form.

Depending on the requirements, the additives are generally provided as spray-dried or freeze-dried, finely divided, free-flowing powders which may contain different proportions of biomass. The bulk density is in particular about 500 $kg/m^3$. The additives are storage-stable.

If the biomass is isolated, naturally other, for example inorganic, solids are also removed. In addition, the additive according to the invention contains at least the greater part of the other substances produced or any added substances which are present dissolved in the fermentation broth, provided they have not been separated by suitable processes.

These substances may include organic secondary products which are produced and excreted by the microorganisms used during fermentation, in addition to D-pantothenic acid. These include L-amino acids chosen from the group L-methionine, L-lysine, L-valine, L-threonine, L-alanine or L-tryptophane, in particular L-valine. Furthermore organic acids which contain up to three carboxyl groups such as e.g. acetic acid, lactic acid, citric acid, malic acid or fumaric acid are also included. Finally sugars which are poorly convertible such as e.g. trehalose, are also included. These compounds are optionally desirable if they contribute to the value of the additive.

Furthermore these substances may include groupings from the convertible sugars used such as e.g. glucose or saccharose.

The invention also provides a process for preparing a feedstuff additive which contains D-pantothenic acid and/or its salts, which is characterised in that
a) a D-pantothenic acid-containing broth which generally contains ammonium salts is prepared by fermentation,
b) the biomass is optionally completely or partly separated from this,
c) the hydroxide or oxide of an alkaline earth or alkali metal is added to the solution or broth obtained in this way, preferably in stoichiometric amounts with respect to the D-pantothenic acid, and
d) the mixture obtained in this way is dried or spray-dried.

The invention also provides a process for preparing a feedstuff additive which contains D-pantothenic acid and/or its salts, is characterised in that
a) a D-pantothenic acid-containing fermentation broth is prepared using sodium, potassium or ammonium hydroxide,
b) the biomass is optionally completely or partly separated from this and
d) the mixture obtained in this way is dried or spray-dried.

Fermentation broths which have been obtained using microorganisms suitable for the production of D-pantothenic acid and which contain D-pantothenic acid and/or its salts are suitable for the process according to the invention.

The microorganisms may be fungi or yeasts such as for example *Debaromyces castellii* or Gram-positive bacteria for example from the genus Corynebacterium or Gram-negative bacteria such as for example those from the Enterobacteriaceae family. The genus Escherichia which includes the species *Escherichia coli* is mentioned in particular from the family of Enterbacteriaceae. Within the species *Escherichia coli*, the so-called K-12 strains such as for example the strains MG1655 or W3110 (Neidhard et al.: *Escherichia coli* and Salmonella. Cellular and Molecular Biology (ASM Press, Washington D.C.)) or *Escherichia coli* wild type strain IF03547 (Institut fur Fermentation, Osaka, Japan) and mutants derived therefrom may be mentioned. Again, among the strains prepared from IF03547, those named FV5069/pFV31 (EP-A-0 590 857) and FV5069/pFV202 (WO 97/10340) are exceptional. The species *Corynebacterium glutamicum* is mentioned in particular from the genus Corynebacterium.

The microorganisms mentioned above may be cultivated continuously or batchwise in a batch process or a fed-batch process or a repeated fed-batch process for the purpose of D-pantothenic acid production. Summaries of known methods of cultivation are given in the textbook by Chmiel (Bioprozesstechnik 1. Einführung in die Bioverfahrenstechnik (Gustav Fischer Verlag, Stuttgart, 1991) or in the textbook by Storhas (Bioreaktoren und periphere Einrichtungen (Vieweg Verlag, Braunschweig/Wiesbaden, 1994).

The culture medium being used must satisfy the requirements of the particular microorganisms in an appropriate manner. Descriptions of culture media for various microorganisms are given in "Manual of Methods for General Bacteriology" produced by the American Society for Bacteriology (Washington D.C., USA, 1981). Sugars and carbohydrates such as e.g. glucose, saccharose, lactose, fructose, maltose, molasses, starch and cellulose, oils and fats such as e.g. soya oil, sunflower oil, peanut oil and coconut fat, fatty acids such as e.g. palmitic acid, stearic acid and linoleic acid, alcohols such as e.g. glycerol and ethanol and organic acids such as e.g. acetic acid may be used as sources of carbon. These substances may be used separately or as a mixture. Organic nitrogen-containing compounds such as peptones, yeast extract, meat extract, malt extract, maize steep liquor, soybean meal and urea or inorganic compounds such as ammonium sulfate, ammonium chloride, ammonium phosphate, ammonium carbonate and ammonium nitrate may be used as sources of nitrogen. The sources of nitrogen may be used separately or as a mixture. Potassium dihydrogen phosphate or dipotassium hydrogen phosphate or the corresponding sodium-containing salts may be used as sources of phosphorus. The culture medium must also contain salts of metals, such as e.g. magnesium sulfate or iron sulfate, which are required for growth. Finally, essential growth-promoting substances such as amino acids and vitamins are also used in addition to the substances mentioned above. In addition, precursors of D-pantothenic acid such as aspartate, β-alanine, ketoisovalerate, ketopantoic acid or pantoic acid and optionally their salts may also be added to the culture medium. The feedstocks mentioned may be added to the culture in the form of a one-off batch or may be fed to the culture in a suitable manner during cultivation.

Ammonia or ammonia water are preferably used to regulate the pH. Other basic compounds such as sodium hydroxide or potassium hydroxide are optionally suitable. If acid compounds are required, phosphoric acid or sulfuric acid are used in an appropriate manner. To control the production of foam, anti-foam agents, such as e.g. fatty acid polyglycol esters, are used. Suitable selectively acting substances e.g. antibiotics are optionally added to the medium to maintain the stability of plasmids. In order to maintain aerobic conditions, oxygen or oxygen-containing gas mixtures such as e.g. air are passed into the culture. The temperature of the culture is normally 20° to 45° and preferably 25° C. to 40° C. The culture procedure is continued until a maximum of D-pantothenic acid has been produced. This target is generally reached within 10 hours to 160 hours.

The fermentation broths obtained in this way generally have a dry weight of 7.5 to 25 wt. % and contain 2 to 20 wt. % of D-pantothenic acid. Fermentation processes in which the D-pantothenic acid amounts to at least 20 wt. % of the dry weight after completion of fermentation are particularly advantageous. It is also advantageous if the fermentation process is performed in a sugar-limited manner, at least at the end, but advantageously over at least 30% of the fermentation time. That means that the concentration of convertible sugars in the fermentation medium is held at or is lowered to ≧0 to 3 g/l during this time.

In a variant which contains ammonium ions for preparing the additive according to the invention, the biomass is optionally initially removed completely or partly from the D-pantothenic acid-containing fermentation broths, by known separation methods such as for example centrifuging, filtering, decanting or a combination thereof. According to the invention, however, it is also possible to leave the entire biomass in the fermentation broth. Finally, 0.8 to 1.2, preferably 0.95 to 1.1 equivalents of an oxide or hydroxide of an alkali or alkaline earth metal, in particular NaOH, KOH, Ca(OH)$_2$ or MgO, with respect to the D-pantothenic acid, is added to this broth. The suspension obtained in this way is concentrated to a maximum of 60 wt. % dry weight. It is also possible to concentrate the fermentation broth first and then add the oxides. The concentrate obtained is then dried for example using a falling film evaporator or a thin layer evaporator or a spray dryer or a freeze-drying unit to give a pourable, free-flowing, finely divided powder.

Furthermore, the inventors have found a new method of preparing ammonium, potassium or sodium D-pantothenic acid-containing powders or forms of presentation which contain these in a rapid and cost-effective manner. For this, a D-pantothenic acid-containing fermentation broth is prepared using the corresponding hydroxyl compound, the biomass is optionally first removed, completely or partly, by known separation methods such as for example centrifuging, filtering, decanting or a combination thereof. According to the invention, however, it is also possible to leave the entire biomass in the fermentation broth. Then the optionally pre-treated broth is concentrated or dried out using known methods such as for example by using a rotary evaporator or a thin layer evaporator or a falling film evaporator. The broth concentrated in this way is then processed to give a preferably pourable, free-flowing, finely divided powder using the methods of spray-drying or freeze-drying or some other process.

The new products according to the invention which contain D-pantothenic acid and/or its salts, which can be prepared by the process described above, contain 20–80 wt. %, preferably 30–75 wt. % of D-pantothenic acid. They generally contain inorganic constituents in an amount of 2.5–25 wt. % and optionally organic secondary products in an amount of $\geq 0$ to 30 wt. %. The proportion of dry biomass amounts to 0 to 35 wt. %. The water content is preferably $\leq 5$ wt. %. The product is used as a feedstuff additive.

The concentration of D-pantothenic acid may be determined using known methods (Velisek; Chromatographic Science 60, 515–560 (1992)).

DETAILED DESCRIPTION OF THE PREFERRED EMBODIMENTS

EXAMPLES

The present invention is explained in more detail in the following by means of working examples. For this purpose, trials were performed with the D-pantothenic acid producing strain *Escherichia coli* 5069/pFV31, which is deposited as FERM-BP 4395, in accordance with the Budapest convention, at the Fermentation Research Institute, Agency of Industrial Science and Technology in 1-1-3, Higashi, Tsukuba-shi, Ibaraki (Japan).

Example 1
Preparing a D-pantothenic Acid-containing Fermentation Broth
1. Preparing the Inoculum A sample of *Escherichia coli* FV5069/pFV31 was painted onto LBG agar which had been supplemented with 50 μg per ml of ampicillin. This agar plate culture was incubated for 17 hours at 37° C. and then stored in a refrigerator at +4° C. Selected individual colonies were then propagated further in LBG broth. LBG broth has the following composition: 10 g/l peptone, 5 g/l yeast extract, 5 g/l NaCl and 1 g/l glucose. LBG agar also contains 12 g/l agar. Ready prepared preparations can be purchased from Gibco/BRL (Paisley, Scotland, Great Britain) as LB broth base or LB agar. After adding 1 g/l glucose, the medium mentioned above is then obtained. Cultures of 10 ml, which were placed in 100 ml conical flasks, were incubated for 16 hours at 37° C. and 180 rpm in an ESR incubator from Kuhner AG (Birsfelden, Switzerland). Then the cell suspension was centrifuged out in a J-6B centrifuge from Beckmann (Hannover, Germany) for 15 minutes at 4000 rpm. The cell pellet was resuspended in 10 ml of LBG medium which had been supplemented with 20% of glycerol and bottled in 10 aliquots of 1 ml each, under sterile conditions and frozen at −70° C. These cultures were used as a master cell bank.

To prepare a working cell bank, LBG medium which had been supplemented with 50 μg/ml of ampicillin, was shared between 100 ml conical flasks in 10 ml portions and then inoculated with 100 μl of the master cell bank described above. The mixtures were incubated for 16 hours at 37° C. and 180 rpm in an ESR incubator from Kuhner AG (Birsfelden, Switzerland). After incubation, the optical density (OD) of the culture suspension was determined using a LP2W photometer from the Dr. Lange Co. (Berlin, Germany) at a measurement wavelength of 660 nm. It was 3.5. Then the cell suspension was placed in sterile 30 ml polyethylene tubes from the Greiner Co, (Frickenhausen, Germany) under sterile conditions, and centrifuged out at 2500 rpm for 15 minutes using a J-6B centrifuge from Beckmann (Hannover, Germany). The separated biomass was resuspended in 10 ml of LBG medium which had been supplemented with 20% of glycerol. Then the cell suspension was placed, in 500 μl portions, in 1 ml sterile (sic) from the Nalgene Co. (New York, U.S.A.) under sterile conditions and frozen at −70° C. The preserved portions prepared in this way were used as a working cell bank.

2. Preparing a D-pantothenic Acid-containing Fermentation Broth

To prepare a pantothenic acid-containing fermentation broth, the working cell bank was first multiplied in a shaking flask culture and this was used to inoculate a prefermenter. The culture from the pre-fermenter was used to inoculate the production fermenter.

SKA medium was used for the shaking flask culture. SKA medium was prepared as described in the following. 7.0 g $(NH_4)_2SO_4$, 0.5 g $KH_2PO_4$, 1.0 g $K_2HPO_4$, 0.5 g $MgSO_4*7H_2O$, 0.01 g $MnSO_4*H_2O$, 0.01 g $ZnSO_4*7H_2O$, 0.005 g $Fe_2(SO_4)_3$, and 20 g of maize steep liquor, which had previously been adjusted to a pH of 6.8 with 25% strength ammonia solution, were weighed into a 1 l glass beaker and then 875 ml of distilled water were added thereto. This maize steep liquor-containing salt solution was sterilised in an autoclave at 121° C. for 20 minutes. Furthermore, a solution consisting of 125 g of distilled water, 28.7 g glucose and 0.002 g thiamine*HCl was sterilised by filtration. 10 g of $CaCO_3$ were weighed into a 100 ml flask and sterilised in an autoclave at 123° C. for 20 minutes. SKA medium was obtained by combining the two components mentioned above with the maize steep liquor-containing salt solution.

This SKA medium was divided into 12.5 ml portions in 100 ml conical flasks and then inoculated with 0.5 ml of a cell suspension. A preserved portion of the working cell culture, diluted 1:100 with sterile physiological saline was used as the cell suspension. Incubation was performed for 20 hours at 32° C. and 150 rpm in a RC-1-TK incubator from Infors AG (Bottmingen, Switzerland). The optical density at a measurement wavelength of 660 nm (OD 660) determined after this procedure was 12.5.

0.5 ml of this shaking flask culture were diluted with 4.5 ml of physiological saline and of that 0.7 ml were used to inoculate 1300 ml of culture medium which had been initially placed in a 2 l laboratory fermenter model Biostat® MD from Braun Diessel Biotech GmbH (Melsungen, Germany).

The culture medium was prepared as follows. A solution consisting of 9.81 g $(NH_4)_2SO_4$, 0.7 g $KH_2PO_4$, 1.402 g $K_2HPO_4$, 0.70 g $MgSO_4*7H_2O$, 0.014 g $MnSO_4*H_2O$, 0.014 g $Fe_2(SO_4)_3$ and 28.04 g maize steep liquor in 1300 ml of tap water was adjusted to a pH of 6.5 with 25% strength ammonia solution and sterilised in an autoclave at 121° C. for 20 minutes. To this maize steep liquor-containing salt solution was added a separate sterile-filtered solution which contained 40.62 g glucose and 0.0042 g thiamine*HCl in 100 g of distilled water, under sterile conditions.

Fermentation was performed for 16 hours at 37° C. and with a rate of aeration of 1 vvm. The dissolved oxygen was kept at 20% and the pH was kept at 6.5. 25% strength ammonia solution was used as the pH regulating agent. The optical density was 13.1. 90 ml of this culture was used to inoculate 1144 ml of growth medium for the main fermentation procedure in a 2 l laboratory fermenter, Biostat® MD model.

The growth medium was prepared as follows. A solution consisting of 4.14 g $(NH_4)_2SO_4$, 0.744 g $KH_2PO_4$, 1.0 g $K_2HPO_4$, 0.83 g $MgSO_4*7H_2O$, 0.0124 g $MnSO_4*H_2O$, 18.87 g β-alanine, 0.74 g Struktol J647 and 49.72 g of maize steep liquor in 1144 ml of tap water was adjusted to a pH of 6.5 with 25% strength ammonia solution and sterilised in an autoclave at 121° C. for 20 minutes. To this maize steep liquor-containing salt solution was added a separate sterile-filtered solution which contained 35.92 g glucose and 0.002 g thiamine*HCl in 100 ml of distilled water, under sterile conditions.

Fermentation was performed for 40 hours at 37° C. In the growth phase the pH was 6.5 and the rate of aeration was 1 vvm. In the production phase the pH was 6.0 and the rate of aeration was 1.5 vvm. The dissolved oxygen was maintained at less than 2% in both phases. The 25% strength ammonia solution was used as the pH regulating agent. During fermentation, production medium 1 and production medium 2 were fed step-wise. Maize steep liquor was added in one portion during cultivation. The production medium (sic) contained 465.29 g glucose and 0.0261 g thiamine*HCl in 584 ml of tap water and had been sterile-filtered. Production medium 2 contained 37.5 g S-alanine in 140 ml of tap water which had been sterilised in an autoclave at 121° C. for 20 minutes. After a fermentation time of 7.5 hours and up to the end of the cultivation stage, production medium 1 was fed stepwise. After 10.5 hours of cultivation, 49.5 g of maize steep liquor which had been dissolved in 100 ml of tap water and sterilised for 20 minutes at 121° C. in an autoclave, were added, under sterile conditions. After a fermentation time of 12.5 hours and up to the end of the cultivation stage, production medium 2 was fed at a rate of addition of 3.5 g/h. After 41 hours of cultivation, a pantothenic acid concentration of 6.1 wt. % was found in the fermentation broth.

The concentration of D-pantothenic acid was determined using a HPLC (high performance liquid chromatography) unit model M321 from Knauer (Berlin, Germany) by means of RI (refractive index) detection using a Hypersil APS2 amino phase with 5 μm particle size.

Example 2

In a fermentation trial which was performed under the same conditions as described in example 1, a pantothenic acid concentration of 5.4 wt. % was detected in the fermentation broth after a cultivation time of 43 hours. The concentration of L-valine was 8 g/l.

Example 3
Preparing Calcium D-pantothenate

The biomass was first separated from a pantothenic acid-containing fermentation broth which had been prepared using the process described in examples 1 and 2 and which contained about 6.1 wt. % of D-pantothenic acid. For this, 1 l of the fermentation broth mentioned above was centrifuged using a laboratory centrifuge, a Biofuge-Stratos model from Heraeus (Dusseldorf, Germany), for 20 minutes at 4,000 rpm and the supernatant centrifuge liquid was purified further by cross-flow ultrafiltration using an MRC polymer membrane of 30 kD in an UF unit from ICT GmbH (Bad Homburg, Germany).

Then 10.1 g of solid $Ca(OH)_2$ (96%; MERCK, Darmstadt, Germany) were added batchwise, with stirring. The pH was then about 10.3. The broth treated in this way was then concentrated under vacuum at 60° C. in a rotary evaporator, a Rotavapor RE-120 from Büchi-Labortechnik GmbH (Konstanz, Germany) to a liquid content of about 50% dry weight. The concentrated broth obtained in this way was then spray-dried to prepare the calcium salt of D-pantothenic acid. For this, a laboratory spray dryer, a Büchi-190 from Büchi-Labortechnik GmbH (Konstanz, Germany), was used with an inlet temperature of 107° C., an outlet temperature or 85° C., a pressure difference of −40 mbar and a rate of flow of air of 600 NL/h.

The calcium D-pantothenate-containing product prepared in this way had a pantothenic acid concentration of 68.5 wt. % was free-flowing and had a bulk density of 460 mg/ml. After being stored for five months, the concentration of D-pantothenic acid was 67.6 wt. %.

Example 4
Preparing Sodium D-pantothenate

The biomass was first separated from a pantothenic acid-containing fermentation broth which had been prepared using the process described in examples 1 and 2 and which contained about 6.1 wt. % of D-pantothenic acid. For this, 1 l of the fermentation broth mentioned above was centrifuged and ultrafiltered in the same way as described in example 2 (sic).

Then 10.6 g of NaOH (99%; MERCK) were added batchwise, with stirring. The pH was then about 10. The broth treated in this way was then concentrated under vacuum at 50–60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold (Cologne, Germany), to prepare the sodium salt of D-pantothenic acid.

The sodium D-pantothenate-containing product prepared in this way had a D-pantothenic acid concentration of 63.8 wt. % and was free-flowing. After being stored for five months, the concentration of D-pantothenic acid was 63.0 wt. %.

Example 5
Preparing Magnesium D-pantothenate

The biomass was first separated from a pantothenic acid-containing fermentation broth which had been prepared using the process described in examples 1 and 2 and which contained about 6.1 wt. % of D-pantothenic acid. For this, 1 l of the fermentation broth mentioned above was centrifuged and ultrafiltered in the same way as described in example 2.

Then 5.4 g of solid MgO (97%; MERCK) were added batchwise, with stirring. The pH was then about 9 to 10. The broth treated in this way was then concentrated under vacuum at 50–60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold, to prepare the magnesium salt of D-pantothenic acid.

The magnesium D-pantothenate-containing product prepared in this way had a D-pantothenic acid concentration of 64.7 wt. % and was free-flowing. After being stored for five months, the concentration of D-pantothenic acid was 64.4 wt. %.

Example 6
Preparing Potassium D-pantothenate

The biomass was first separated from a pantothenic acid-containing fermentation broth which had been prepared using the process described in examples 1 and 2 and which contained about 6.1 wt. % of D-pantothenic acid. For this, 1 l of the fermentation broth mentioned above was centrifuged and ultrafiltered in the same way as described in example 2.

Then 17.4 g of KOH (85%; MERCK) were added batchwise, with stirring. The pH was then about 10 to 11. The broth treated in this way was then concentrated under vacuum at 60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold, to prepare the potassium salt of D-pantothenic acid.

The potassium D-pantothenate-containing product prepared in this way had a D-pantothenic acid concentration of 63.5 wt. % and was free-flowing. After being stored for five months, the concentration of D-pantothenic acid was 62.9 wt. %.

Example 7
Preparing Ammonium D-pantothenate

The biomass was first separated from a pantothenic acid-containing fermentation broth which had been prepared using the process described in examples 1 and 2 and which contained about 6.1 wt. % of D-pantothenic acid. For this, 1 l of the fermentation broth mentioned above was centrifuged and ultrafiltered in the same way as described in example 2.

The broth treated in this way was then concentrated under vacuum at 60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold, to prepare the ammonium salt of D-pantothenic acid.

The ammonium D-pantothenate-containing product prepared in this way had a D-pantothenic acid concentration of 66.8 wt. % and was free-flowing.

Example 8
Preparing Calcium D-pantothenate From a Biomass-containing Fermentation Broth A pantothenic acid-containing fermentation broth which had been prepared using the method described in examples 1 and 2 and which contained about 6.1 wt. % of D-pantothenic acid was first concentrated under vacuum at 60° C. in a rotary evaporator, a Rotavapor RE-120 from Büchi-Labortechnik GmbH (Konstanz, Germany) a volume of 1.0 l to a liquid concentration of about 30% dry weight. Then 10.1 g of solid Ca(OH)$_2$ (96%; MERCK, Darmstadt, Germany) were added batchwise, with stirring. The pH was then about 10. The biomass-containing broth treated and concentrated in this way was then spray-dried to prepare the calcium salt of D-pantothenic acid. For this, a laboratory spray dryer, a Büchi-190 from Büchi-Labortechnik GmbH (Konstanz, Deutschland), was used with an inlet temperature of 107° C., an outlet temperature of 85° C., a pressure difference of −40 mbar and a rate of flow of air of 600 NL/h.

The calcium D-pantothenate-containing product prepared in this way had a concentration of D-pantothenic acid of 9.8 wt. %, was free-flowing and had a bulk density of 80 mg/ml. The biomass content was about 30 wt. %.

What is claimed is:

1. Animal feedstuff additive which contains at least one member selected from the group consisting of D-pantothenic acid and salts thereof and which is obtained from a fermentation broth, said additive comprising:

a) at least one member selected from the group consisting of D-pantothenic acid and salts thereof, b) 0 to 100% of a biomass formed during fermentation of microorganisms which produce the D-pantothenic acid, and c) dissolved ingredients of the fermentation broth, wherein d) the additive is present in a solid, finely divided and free-flowing form.

2. Animal feedstuff additive according to claim 1, comprising one or more alts selected from the group consisting of sodium, potassium, ammonium, magnesium and calcium salts of D-pantothenic acid.

3. Animal feedstuff additive according to claim 1, wherein the amount of D-pantothenic acid and salts thereof is 20 to 80 wt. % (dry weight).

4. Animal feedstuff additive according to claim 1, comprising spray-dried powders.

5. Animal feedstuff additive according to claim 1, further comprising one or more L-amino acids selected from the group consisting of L-methionine, L-lysine, L-valine, L-alanine, L-threonine and L-tryptophane.

6. A process for preparing feedstuff additive which contains at least one member selected from the group consisting of D-pantothenic acid and salts thereof, comprising:

a) obtaining a D-pantothenic acid-containing fermentation broth which contains ammonium salts and is obtained by fermentation, b) optionally at least partially removing biomass from the fermentation broth;

c) adding a hydroxide or oxide of an alkaline earth metal or alkali metal to the solution or broth obtained in step b), and d) drying the mixture obtained in step c).

7. A process according to claim 6, comprising:

adding the oxide or hydroxide in a stoichiometric ratio of 0.8 to 1.2, with respect to the D-pantothenic acid.

8. A process for preparing feedstuff additive which contain at least one member selected from the group consisting of D-pantothenic acid and sodium, potassium or ammonium salts thereof, comprising:

a) obtaining a D-pantothenic acid-containing broth using corresponding hydroxyl compounds, b) optionally at least partially removing biomass from the broth, c) optionally concentrating the mixture obtained, and d) drying to obtain the feedstuff additive which contains corresponding pantothenate.

9. The process according to claim 6, wherein the drying step comprises spray drying.

10. The process according to claim 7, wherein the oxide or hydroxide is added in a stoichiometric ratio of 0.95 to 1.1, with respect to the D-pantothenic acid.

11. The process according to claim 8, wherein the drying step comprises spray drying.

* * * * *